(12) United States Patent
Benhamou

(10) Patent No.: US 9,381,073 B2
(45) Date of Patent: Jul. 5, 2016

(54) ASSEMBLY OF A DENTAL IMPLANT AND A PROSTHETIC ELEMENT

(75) Inventor: Olivier Benhamou, Brussels (BE)

(73) Assignee: SUDIMPLANT, Toulouse (FR)

( * ) Notice: Subject to any disclaimer, the term of this patent is extended or adjusted under 35 U.S.C. 154(b) by 0 days.

(21) Appl. No.: 13/575,808

(22) PCT Filed: Jan. 28, 2011

(86) PCT No.: PCT/EP2011/051269
§ 371 (c)(1),
(2), (4) Date: Jan. 4, 2013

(87) PCT Pub. No.: WO2011/092315
PCT Pub. Date: Aug. 4, 2011

(65) Prior Publication Data
US 2013/0209960 A1    Aug. 15, 2013

(30) Foreign Application Priority Data

Jan. 28, 2010 (EP) .................................... 10290044

(51) Int. Cl.
*A61C 8/00* (2006.01)
*A61C 3/02* (2006.01)

(52) U.S. Cl.
CPC ............. *A61C 8/0075* (2013.01); *A61C 3/02* (2013.01); *A61C 8/0001* (2013.01); *A61C 8/006* (2013.01); *A61C 8/008* (2013.01); *A61C 8/0012* (2013.01); *A61C 8/0018* (2013.01); *A61C 8/0022* (2013.01); *A61C 8/0053* (2013.01); *A61C 8/0069* (2013.01); *A61C 8/0074* (2013.01); *A61C 8/0087* (2013.01); *A61C 8/0089* (2013.01); *A61C 8/0056* (2013.01)

(58) Field of Classification Search
CPC .... A61C 8/0089; A61C 8/005; A61C 8/0054; A61C 8/006; A61C 8/0074; A61C 8/0022; A61C 8/075; A61C 3/02; A61C 8/0001; A61C 8/0012; A61C 8/0018; A61C 8/0053; A61C 8/0069; A61C 8/008; A61C 8/0087; A61C 8/0056
USPC .................................. 433/172–176, 165–166
See application file for complete search history.

(56) References Cited

U.S. PATENT DOCUMENTS

| 5,194,000 | A | * | 3/1993 | Dury | .............................. 433/173 |
| 5,259,398 | A | * | 11/1993 | Vrespa | .......................... 128/898 |
| 5,961,328 | A | | 10/1999 | Somborac et al. | |
| 6,206,696 | B1 | * | 3/2001 | Day | .............................. 433/141 |

(Continued)

FOREIGN PATENT DOCUMENTS

EP          1452149 A1 * 9/2004  ............... A61C 8/00
WO       WO 01/80768        11/2001

*Primary Examiner* — Heidi M Eide
(74) *Attorney, Agent, or Firm* — Jacobson Holman PLLC

(57) ABSTRACT

Assembly having a dental implant and a prosthetic element, which dental implant comprises a body arranged to be implanted in the jawbone, which prosthetic element comprises an intra-implant part and an extra-implant part, said body comprising an internal cavity intended to receive the intra-implant part of the prosthetic element, said prosthetic element being a single-piece element the intra-implant part of which is formed by a tenon, arranged to be sealed or glued in the cavity, and the extra-implant part of which is configured in the form of an attachment member arranged so as to apply a dental prosthesis directly thereto, said intra-implant part having an essentially smooth wall provided with at least one discharge groove.

18 Claims, 4 Drawing Sheets

(56) References Cited

U.S. PATENT DOCUMENTS

| | | |
|---|---|---|
| 6,273,720 B1 | 8/2001 | Spalten |
| 6,464,500 B1 | 10/2002 | Popovic |
| 2005/0136378 A1* | 6/2005 | Ennajimi et al. ............... 433/173 |
| 2009/0136899 A1* | 5/2009 | Porter et al. .................. 433/174 |
| 2010/0196851 A1* | 8/2010 | Konig ............................ 433/173 |
| 2011/0065064 A1* | 3/2011 | Kahdemann et al. ......... 433/174 |

* cited by examiner

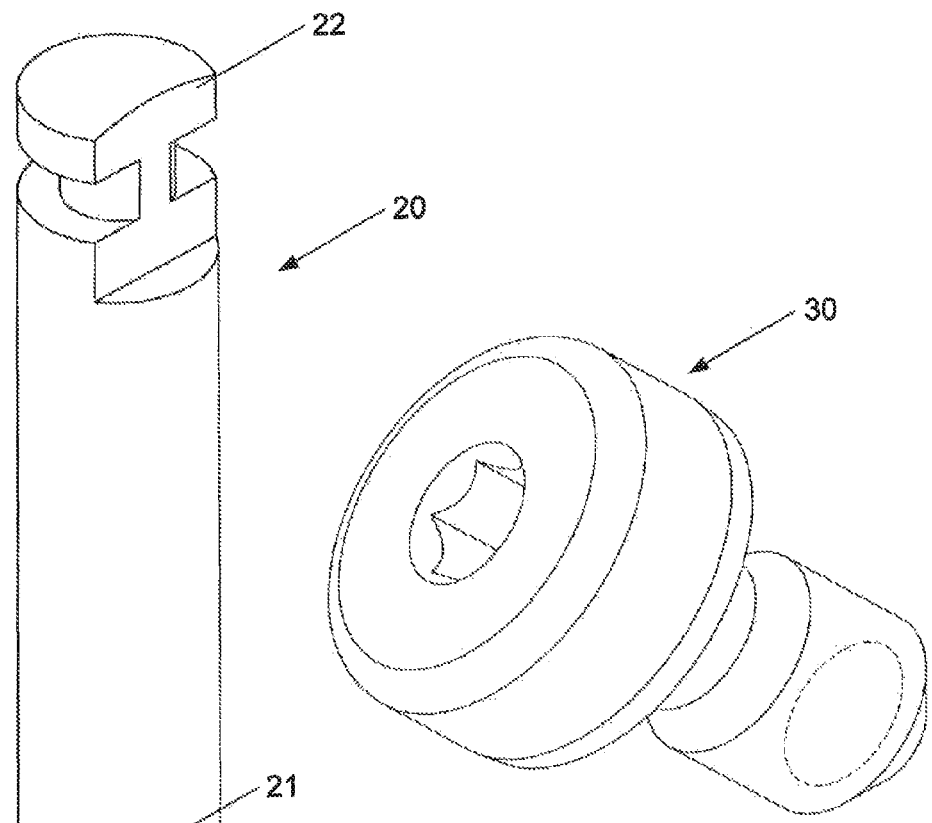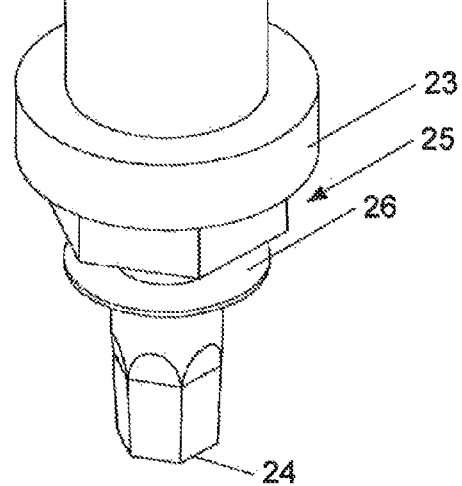

ASSEMBLY OF A DENTAL IMPLANT AND A PROSTHETIC ELEMENT

This is a 371 of PCT/EP11/051269 filed Jan. 28, 2011, which has a priority of European no. 10290044.6 filed Jan. 28, 2010, hereby incorporated by reference.

The present invention concerns an assembly having a dental implant and a prosthetic element, which dental implant comprising a body arranged to be implanted in the jawbone, which prosthetic element comprising an intra-implant part and an extra-implant part, said body comprising an internal cavity intended to receive the intra-implant part of the prosthetic element, said prosthetic element being a single-piece element the intra-implant part of which is formed by a tenon arranged to be sealed or glued in the cavity, and the extra-implant part of which is configured in the form of an attachment member arranged so as to apply a dental prosthesis directly thereto.

Such an assembly is known from the patent U.S. Pat. No. 5,961,328. According to the known assembly, the implant comprises a body having a cavity in which a prosthetic element is placed, formed by a frustoconical part or false stump or attachment system. Subsequently, a dental crown will be sealed on this false stump or a removable prosthesis will be clipped onto the attachment system.

A dental implant is an artificial root, the role of which is to replace a natural tooth root. The surgical fitting thereof consists of producing, by drilling in the jawbone, an alveolus in which the implant will be screwed or impacted. After a healing time of several weeks, this implant can be brought into function by fitting a prosthetic component that will support a crown.

There exist two surgical approaches: a technique of two operating times, where the implant is buried in the bone and covered by the gum during the bone healing time. Once this bone healing has ended, during a second operating time, the gum above the implant will be incised in order to render the implant accessible and to fix thereto a healing screw provided to pass through the gum, and thus enabling the gum to heal. In this case, the gum will heal around this healing screw rather than around the implant. After gum healing, this screw is removed and replaced by a prosthetic element on which the crown will be fixed. In this case, second-intention healing at the gum level is spoken of.

The technique in one operating time consists of fitting an implant of a different design since it will have both an endobone part and a transgingival part. In this configuration, healing of the gum by first intention will be obtained around the transgingival part of the implant. Crimping, referred to as epithelial attachment, is acquired definitively in this technique. This technique, where the implant is from the outset in relationship with the buccal cavity, therefore does not involve a second operating time.

By using a single-piece prosthetic element (non-transcrewed system) the aforementioned principle used in conventional odontology has been transposed to oral implantology. This is because the single-piece element can, by virtue of its intra-implant part, easily be introduced into the cavity of the dental implant, in the same way as in conventional odontology. In addition, since the extra-implant part is configured in the form of an attachment member, the dental surgeon can, without any additional skill, apply the dental prosthesis thereto, for example in the form of a crown.

A drawback of the known assembly is however that the bonding or sealing requires both suitably viewing the setting area, and the presence of a "reservoir" for recovering the excess cement or adhesive, which makes the implantation complex and requires time.

The aim of the invention is to simplify the dental implant installation and to offer an assembly comprising of a dental implant and a prosthetic element where the prosthetic element can be installed by a dental surgeon without the latter being a specialist in this matter.

To this end, an assembly according to the invention is characterized in that said intra-implant part has an essentially smooth wall provided with at least one groove. The essentially smooth wall enables a bonding or sealing technique to be used for fixing the prosthetic element in the cavity, whereas the discharge groove enables excess cement or adhesive and air to be cleared during sealing or bonding. In this way, a clearing area entirely clean of excess cement or adhesive and regulatory sealing or bonding of the intra-implant part are obtained.

A first preferential embodiment of an assembly according to the invention is characterized in that said cavity comprises an entry section configured in a polygon, and in that said prosthetic element comprises, at the junction between the intra- and extra-implant parts, a junction part configured as a polygon so that the junction part can fit in the entry section. The configuration as a polygon of the entry section and a segment of the prosthetic element prevents the latter from turning when it is introduced into the cavity. This is because, since the junction part of the prosthetic element matches the polygon configuration of the entry section, the fitting of this junction part in the entry section will result in their positions being fixed, thus preventing the rotation of the prosthetic element in the cavity.

A second preferential embodiment of an assembly according to the invention is characterized in that said cavity comprises an internal tapping that extends over at least part of the depth of the cavity. This tapping makes it possible to screw a healing or covering screw therein.

A third preferential embodiment of an assembly according to the invention is characterized in that said cavity comprises a retention groove applied in its internal wall and arranged to receive an ancillary element forming part of a spindle arranged to hold said implant. This considerably facilitates the fitting of an implant.

A fourth preferential embodiment of an assembly according to the invention is characterized in that the extra-implant part has a frustoconical geometry. This enables the dental prosthesis to be fitted.

A fifth preferential embodiment of an assembly according to the invention is characterized in that the extra-implant part is provided with an attachment element. This affords stabilization of the removable apparatus.

A sixth preferential embodiment of an assembly according to the invention is characterized in that said implant is fabricated either from metal or ceramic or a composite material or PEEK, or a combination of these materials, said prosthetic element is fabricated either from metal, or ceramic, or PEEK, or a calcinable material, or a composite material or a combination of these materials. In particular the use of a calcinable material allows wide flexibility in implementation.

A seventh preferential embodiment of an assembly according to the invention is characterized in that said drill has a first and second blade disposed substantially perpendicular to each other, one end of the second blade being offset with respect to an end of the first blade. This affords better drilling in the jawbone.

An eighth preferential embodiment of an assembly according to the invention is characterized in that one end of the spindle is configured in a polygon and arranged to be introduced into the entry section of the cavity. Thus this end of the spindle perfectly matches the shape of the entry section of the cavity, which facilitates the fitting of the dental implant.

The invention will now be described in more detail with the help of the drawings, which illustrate preferential embodiments of an assembly according to the invention. In the drawings:

FIG. 1 shows an external view of a dental implant forming part of an assembly according to the invention, FIG. 2 shows a view in section in the longitudinal direction of the dental implant illustrated in FIG. 1;

FIGS. 3a and b illustrate a stump forming part of an assembly according to the invention;

FIG. 4 illustrates a spindle forming part of the assembly;

FIG. 5 illustrates a covering screw forming part of the assembly;

In the same drawings, the same reference has been attributed to the same element or to a similar element.

Figure 1:
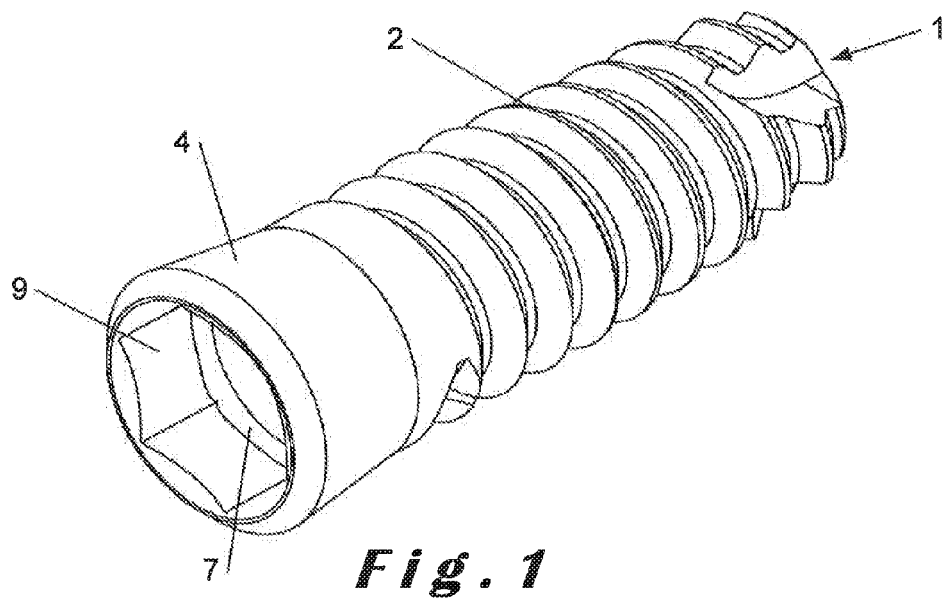
Figure 3:
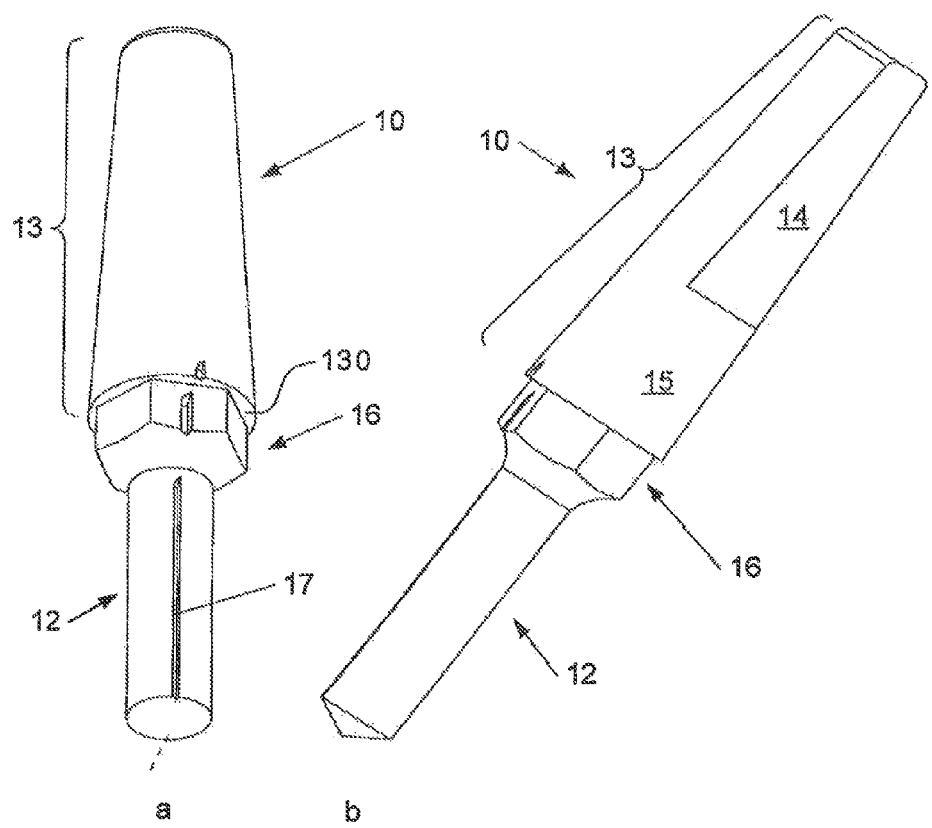

The assembly according to the invention comprises a dental implant 1 (see FIG. 1) and a prosthetic element 10 (see FIG. 3). The dental implant 1 illustrated in FIG. 1 comprises a body arranged to be implanted and having a cylindro-conical form with preferably a conicity of 4 mm at the apex, including 2.35 mm of cruciform base, with a neck 4 presenting a splayed part to a height of 2 mm. The diameter at the neck 4 may range from 2.5 to 7 mm, but more particularly between 2.9 and 5.7 mm. The length of the dental implant ranges from 5 to 17 mm, in particular from 6 to 15.5 mm. Apart from the cylindro-conical shape, a cylindrical shape may also be envisaged. The dental implant illustrated in FIG. 1 may be used both for a so-called two operating times technique or for a so-called one operating time technique. For this purpose, the neck 4 will be buried not in the bone but rather in the gum after the fitting of the dental implant during the use of the so-called one-time technique, whereas this same splayed part will be buried in the bone during use of the so-called two-time technique. The external wall of the dental implant comprises a tapping 2 for screwing the dental implant into the jawbone.

The dental implant 1 is for example manufactured from metal, such as titanium, zirconia or a zirconia-titanium hybrid. It may also be manufactured from PEEK, ceramic or a composite material, or a combination of these materials.

Figure 2:
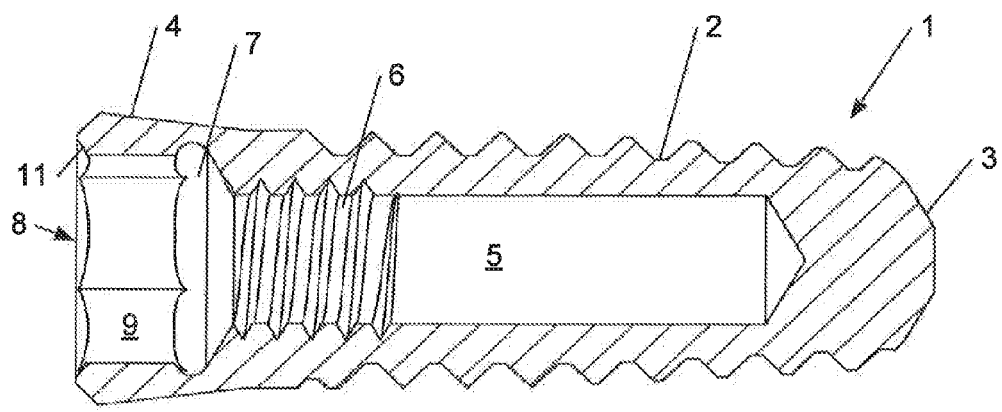

FIG. 2 illustrates a view in section in the longitudinal direction of a dental implant according to the invention. The body of the dental implant comprises an internal cavity 5, having an entry section 8, situated in the neck 4 of the implant. This entry section 8 is configured in a polygon 9, in particular in a hexagon. It goes without saying that polygon configurations other than a hexagon can be envisaged. The hexagon nevertheless has the advantage in that it allows the use of conventional tools such as a chuck or an Allen key. Preferably, this polygon configuration has the same size, whatever the size of the dental implant, thus making it possible to use the same instrument for fitting the dental implant.

Figure 6:
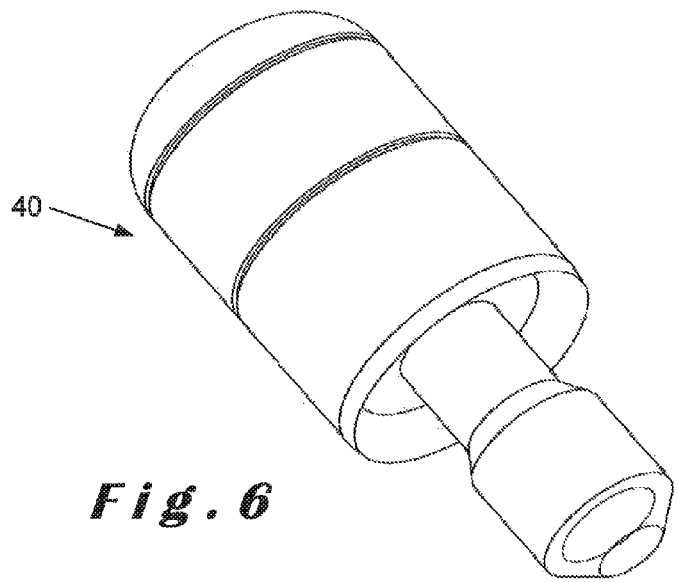
FIG. 6 illustrates a healing screw forming part of the assembly.

Just below this polygon configuration 9 there is situated a retention groove 7 applied in the internal wall of the cavity and arranged to receive a part of a spindle holding the implant, as will be described in detail below. This retention groove preferably has a height of 0.5 mm and is placed between the entry section and an internal tapping 6, which extends inside the cavity 5 over at least part of the depth of the cavity. The internal tapping 6 serves to receive the screw thread of a covering screw as illustrated in FIG. 5, or a healing screw as illustrated in FIG. 6. If the internal tapping serves only to receive a covering or healing screw, it extends over a length of approximately 3 mm and has for example an M2 or M2.5 thread. On the other hand, the internal thread can also be used for screwing the prosthetic element therein, in which case the internal tapping will extend over a distance situated between 0.2 and 15 mm.

The internal cavity 5 extends over a distance situated between 3 and 15 mm, more particularly between 7 and 11 mm, and has a diameter of between 1 and 4 mm. Preferably, the neck 4 of the implant 4 has a smooth surface condition, because of the possibility of burying or not in the bone, thus avoiding a retention of bacterial plaque. On the other hand, the part provided with an external thread 2 will preferably have a rough surface condition in order to improve the integration of the implant in the bone. Preferably, the splayed part 4 of the neck 4 of the implant comprises a bevel 11 that is configured so as to join the prosthetic element when mounted in the dental implant. This affords a good seating for the future prosthesis.

FIGS. 3a and b illustrate a preferential embodiment of a prosthetic element forming part of an assembly according to the invention. The single-piece prosthetic element 10 is for example formed by a false stump in its extra-implant part 13 having a proximal flange 130 and by a cylindrical tenon with a groove in its intra-implant part 12. The intra-implant part is arranged so as to be introduced into the cavity 5 of the dental implant. The intra-implant part is formed by a tenon arranged so as to be sealed or bonded in the cavity. The tenon is preferably cylindrical in shape, but may also have other shapes such as rectangular, hexagonal, conical or cylindro-conical. Where applicable, the prosthetic element may, in its intra-implant part, be provided with a screw thread compatible with the internal tapping present in the cavity 5.

The single-piece prosthetic element is configured in its extra-implant part in the form of a false stump 14-15, arranged so as to receive a dental implant therein directly. This false stump is for example formed by a flat 14 applied to the stump. This flat forms part of a frustoconical geometry of the extra-implant part and extends only over part of approximately two thirds of the height of this extra-implant part. This flat provides anti-rotational locking of the prosthesis.

The single-piece prosthetic element comprises, extending from the proximal flange at the junction between the intra- and extra-implant parts, preferably a junction part 16 configured in a polygon, so that the junction part can fit in the entry section 8 of the cavity, also configured in a polygon 9. Thus, when the two polygon configurations are fitted one in the other, when the prosthetic element is fitted in the dental implant, a rotation of this prosthetic element in the cavity will be prevented by virtue of the gripping of the polygon of the stump in the polygon of the entry section of the implant.

The intra-implant part of the prosthetic element has an essentially smooth wall and is provided with a discharge groove 17 that extends over the entire length of this intra-implant part. The groove 17 is preferably extended over the junction part 16 and past the proximal flange over a distance of less than 1 cm on the extra-implant part. The function of this discharge groove will be described below.

The prosthetic element is preferably manufactured from metal such as for example titanium. It may also be manufactured from ceramic, PEEK or a calcinable material or a combination of these materials. Preferably, the stump has a base of 2.5 to 8 mm with a height situated between 5 and 15 mm for the extra-implant part and between 3 and 15 mm for the intra-implant part.

The single-piece prosthetic element is sealed or bonded in the cavity. For this purpose, a dental cement or adhesive is used that will be applied to the intra-implant part before introducing the prosthetic element in the cavity of the dental implant. This prosthetic element is slid into the cavity and the excess cement or adhesive as well as the air present in the cavity can be released by virtue of the presence of the discharge grooves 17. After having sealed or bonded this single-piece prosthetic element, the dental prosthesis can be fixed at its extra-implant part.

FIG. 4 illustrates a spindle 20 forming part of an assembly according to the invention. The spindle enables the dental implant 1 to be gripped and fitted. The spindle 20 comprises a coupling member 22 used for coupling thereto a contra-angle attachment or a hand-piece for manipulating the spindle, The latter also comprises a rod 21 that is extended first of all in a thicker part 23 and then in a gripping head 25 that is configured in a polygon. This polygon configuration joins the one that is situated in the entry section 8 of the dental implant 1, so that the head 25 can engage in the polygon configuration of the dental implant, thus making it possible to drive the dental implant in order to screw it into the jawbone by means of the spindle.

The spindle 20 also comprises a small disc 26 offset with respect to the part 25 configured in a polygon. The small disc is sized so as to be able to come to be housed in the retention groove 7 of the dental implant. This makes it possible to temporarily fix the dental implant to the spindle 20 when the dental implant is introduced into the mouth of a patient by means of the spindle 20. The small disc 26 is preferably manufactured from a semi-rigid material such as silicone, rubber or PEEK, thus giving flexibility to the small disc 26, which makes it possible not only to easily introduce it into the retention groove 7, but also to bring it out after the dental implant is fitted.

The spindle 20 also preferably comprises at its end a gripping element 24 arranged to engage in a covering screw 30 or a healing screw 40 as illustrated in FIG. 5 or 6. The gripping element 24 is for this purpose configured for example as a hexagonal polygon or as a flat or cruciform screwdriver depending on what is used for the covering 30 or healing 40 screws. Thus the dental surgeon can use the same spindle 20 for gripping the dental implant or implanting it in the jawbone, and its ability to screw the covering 30 or healing 40 screw, which avoids having each time to take another instrument.

Preferably, the assembly according to the invention also comprises the covering screw 30 shown in FIG. 5 and/or the healing screw 40 shown in FIG. 6. These screws are provided with a screw thread arranged to be screwed into the tapping. The form of the covering or healing screw makes it possible to cover the neck 4 of the implant and its bevel 11.

Figure 7:
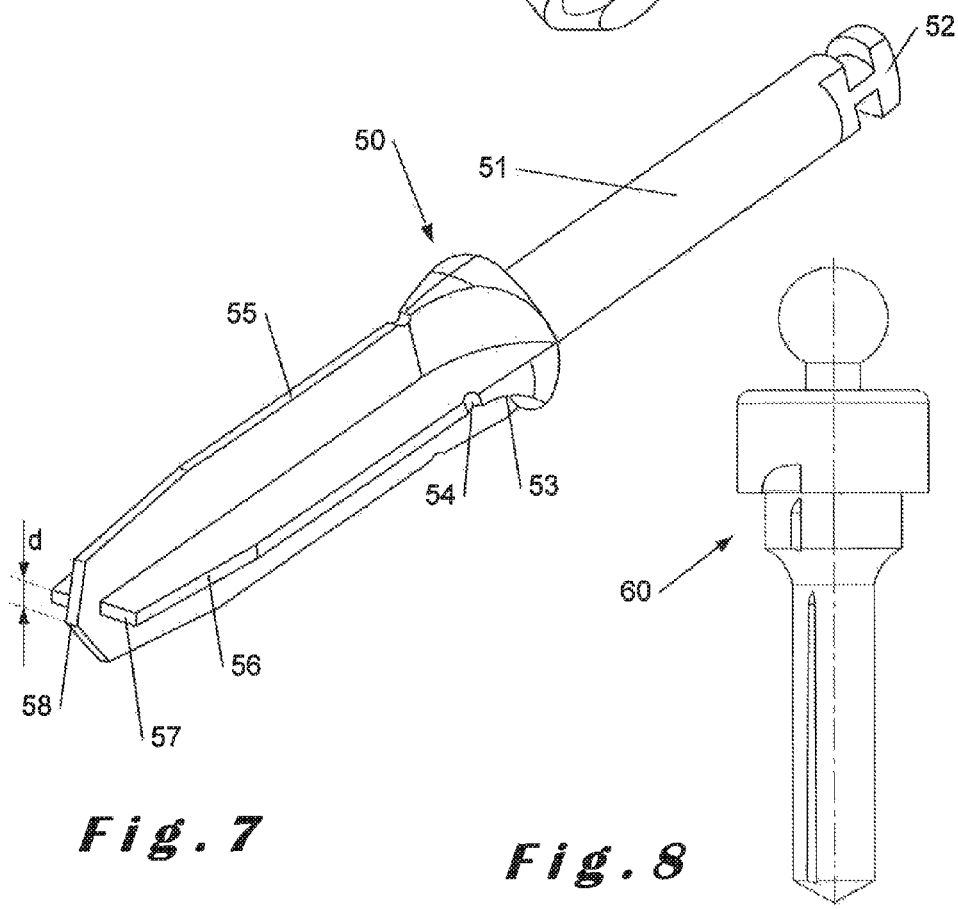
FIG. 7 illustrates a drill forming part of the assembly.

FIG. 7 illustrates an example of a drill 50 preferably forming part of an assembly according to the invention. Just like the spindle 20, the drill 50 comprises a coupling member 52 and a rod 51. The drill 50 has a profile matching that of the dental implant, which makes it possible to drill into the jawbone to the dimension corresponding to that of the dental implant. This makes it possible to use the same drill 50 for the so-called one-time technique and the so-called two-time technique. The reamer 53 makes it possible to drill more deeply, this making it possible to sink the splayed part of the neck 4 of the dental implant into the jawbone.

As illustrated in FIG. 7, the drill comprises a first 55 and second 56 blade placed substantially perpendicular to each other. One end 57 of the second blade being offset d with respect to an end 58 of the first blade. This offset d procures a better cutting effect during drilling into the jawbone since the first blade 55 serves as a leading blade while the second blade 57 serves more for boring out the hole to be drilled. Preferably, the drill has a cylindro-conical shape thus matching that of the dental implant to be fitted. The drill preferably comprises a reamer 53 placed above the blades.

The drill has a diameter preferably lying between 2 and 7 mm, more particularly between 2.7 and 6 mm. It is manufactured from stainless steel, titanium or ceramic. The drill preferably comprises a mark 54 situated between the reamer 53 and the blades 55 and 56, thus enabling the user to identify its drilling limit according to the choice of his implant technique, in one or two operating times.

Figure 8:
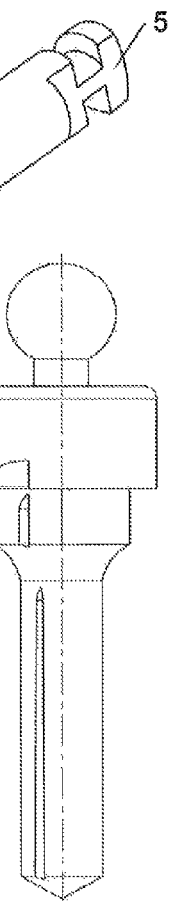
FIG. 8 illustrates an attachment element forming part of the assembly.

FIG. 8 illustrates a spherical attachment 60 where the shape of the shoulder makes it possible to cover the neck of the implant. Thus this spherical attachment can not only be sealed or bonded in the dental implant but can also be used as an element for stabilizing a removable prosthesis.

The invention claimed is:

1. Assembly having a dental implant and a prosthetic element, wherein the dental implant comprises a body arranged to be implanted in the jawbone, the body of the dental implant comprising an internal cavity containing an entry section configured as a polygon, and wherein the prosthetic element comprises a single-piece element having an outer surface with an intra-implant part, an extra-implant part having a proximal flange, and a junction part extending from the proximal flange between the intra- and extra-implant parts, the junction part configured as a polygon matching the entry section polygon so that the junction part is provided to fit in the entry section, the intra implant part of the prosthetic element having an essentially smooth wall and comprising a cylindrically shaped tenon arranged to be sealed or glued in the internal cavity of the body of the dental implant, the extra-implant part of the prosthetic element being configured in the form of an attachment member arranged so as to apply a dental prosthesis directly thereto, the outer surface of the prosthetic element having recessed therein at least one discharge groove extending over the entire length of the intra-implant part, over the entire junction part, and past the proximal flange over a distance of less than 1 cm of the extra-implant part.

2. Assembly according to claim 1, characterized in that the internal cavity further comprises an internal tapping that extends over at least part of a depth of the internal cavity.

3. Assembly according to claim 2, characterized in that the internal cavity further comprises a retention groove applied in an internal wall of the internal cavity and arranged to receive a small disc forming part of a spindle arranged to hold the dental implant.

4. Assembly according to claim 3, characterized in that the retention groove is placed between the entry section and the internal tapping of the internal cavity.

5. Assembly according to claim 2, characterized in that the assembly also comprises a covering screw having a screw thread arranged so as to be screwed into the internal tapping and a spindle having a gripping head configured in a polygon and arranged to be introduced into the entry section of the internal cavity.

6. Assembly according to claim 5, characterized in that the assembly further comprises a healing screw having a screw thread arranged to be screwed into the tapping and in that the spindle comprises an end provided with a gripping element arranged to engage in the covering screw or the healing screw.

7. Assembly according to claim 2, characterized in that the assembly also comprises a healing screw having a screw thread arranged to be screwed into the internal tapping.

8. Assembly according to claim 3, characterized in that the assembly further comprises a spindle having a gripping head arranged so as to be inserted into the retention groove of the internal cavity of the dental implant.

9. Assembly according to claim 1, characterized in that the at least one groove extends over the extra-implant part over a distance of between 2 and 3 mm.

10. Assembly according to claim 1, characterized in that the dental implant has an essentially cylindro-conical geometry, the internal cavity extending coaxially with a central axis of the dental implant.

11. Assembly according to claim 1, characterized in that the extra-implant part has a frustoconical geometry.

12. Assembly according to claim 11, characterized in that the extra-implant part is beveled over part of its length.

13. Assembly according to claim 1, characterized in that the extra-implant part is provided with a spherical attachment having a shoulder shaped to cover the entry section.

14. Assembly according to claim 1, characterized in that said implant is manufactured either from metal, or a ceramic, or a composite material, or PEEK, or a combination of these materials, said prosthetic element is manufactured either from metal, or ceramic, or PEEK, or a calcinable material, or a composite material, or a combination of these materials.

15. Assembly according to claim 1, characterized in that the assembly also comprises a drill having a profile matching that of the dental implant.

16. Assembly according to claim 15, characterized in that the drill comprises a top part provided with a reamer.

17. Assembly according to claim 15, characterized in that the drill comprises first and second blades placed substantially perpendicular to each other, one end of the second blade being offset with respect to an end of the first blade.

18. Assembly according to claim 1, characterized in that the assembly further comprises a spindle having a gripping head configured in a polygon and arranged to be introduced into the entry section of the internal cavity.

* * * * *